(12) United States Patent
Smith

(10) Patent No.: US 10,980,708 B2
(45) Date of Patent: Apr. 20, 2021

(54) SYSTEMS, METHODS AND KITS FOR CLEANSING AN OCULAR REGION

(71) Applicant: OCuSOFT, Inc., Rosenberg, TX (US)

(72) Inventor: Troy Smith, Richmond, TX (US)

(73) Assignee: OCUSOFT, INC., Rosenberg, TX (US)

( * ) Notice: Subject to any disclaimer, the term of this patent is extended or adjusted under 35 U.S.C. 154(b) by 415 days.

(21) Appl. No.: 16/105,726

(22) Filed: Aug. 20, 2018

(65) Prior Publication Data

US 2018/0353377 A1    Dec. 13, 2018

Related U.S. Application Data

(60) Division of application No. 14/707,187, filed on May 8, 2015, now Pat. No. 10,076,465, which is a continuation-in-part of application No. 14/274,198, filed on May 9, 2014, now abandoned.

(51) Int. Cl.
*A61F 9/00* (2006.01)
*A61H 35/02* (2006.01)
*A61K 9/00* (2006.01)

(52) U.S. Cl.
CPC ............ *A61H 35/02* (2013.01); *A61F 9/0008* (2013.01); *A61H 2201/0153* (2013.01); *A61K 9/0048* (2013.01)

(58) Field of Classification Search
CPC . A61F 9/0008; A61F 9/00; A61H 2201/0153; A61H 35/02; A61K 9/0048; A61P 27/02
See application file for complete search history.

(56) References Cited

U.S. PATENT DOCUMENTS

| | | | |
|---|---|---|---|
| 4,904,698 | A | 2/1990 | Adkins, Jr. |
| 6,112,900 | A | 9/2000 | Adkins, Jr. |
| 6,726,386 | B1 | 4/2004 | Gruenbacher et al. |
| 7,951,387 | B2 | 5/2011 | Witham et al. |
| 8,202,853 | B2 | 6/2012 | Adkins, Jr. |
| 8,334,134 | B2 | 12/2012 | Young et al. |
| 8,420,385 | B2 | 4/2013 | Young et al. |
| 9,274,029 | B2 | 3/2016 | Young et al. |
| 9,279,747 | B2 | 3/2016 | Young et al. |

(Continued)

FOREIGN PATENT DOCUMENTS

WO    2013156808 A1    10/2013

OTHER PUBLICATIONS

Extended European Search Report dated Oct. 13, 2017 for related and co-pending EP application No. 15789029.4.

(Continued)

*Primary Examiner* — Kai H Weng
(74) *Attorney, Agent, or Firm* — D'Ambrosio & Menon, PLLC; Usha Menon

(57) ABSTRACT

Systems, methods, and kits useful for cleansing the eyelids and maintaining eyelid hygiene are disclosed. In one embodiment, a system for treating or cleansing an ocular region is disclosed. The system consists essentially of: (A) a tubular applicator, wherein the applicator comprises: (i) a first chamber and a second chamber; and (ii) a sealable element situated between the first chamber and the second chamber, wherein at least the second chamber is substantially pre-filled with an ocular composition, and (B) a dispenser, wherein the dispenser is bonded to an external surface of a first end of the applicator.

9 Claims, 2 Drawing Sheets

(56) References Cited

U.S. PATENT DOCUMENTS

| | | |
|---|---|---|
| 2003/0213820 A1 | 11/2003 | Sherk, Jr. et al. |
| 2006/0246013 A1 | 11/2006 | Adkins, Jr. |
| 2009/0137533 A1 | 5/2009 | Adkins, Jr. |
| 2009/0152296 A1 | 6/2009 | May |
| 2009/0300864 A1 | 12/2009 | Adkins, Jr. et al. |
| 2009/0317503 A1 | 12/2009 | Adkins, Jr. |
| 2011/0017633 A1* | 1/2011 | Holstein ................. A61F 17/00 206/570 |
| 2011/0270220 A1 | 11/2011 | Genosar |
| 2012/0121694 A1 | 5/2012 | Adkins, Jr. et al. |
| 2014/0117040 A1 | 5/2014 | May |

OTHER PUBLICATIONS

International Search Report and Written Opinion dated Sep. 8, 2015 for related PCT application No. PCT/US2015/29889.

* cited by examiner

SYSTEMS, METHODS AND KITS FOR CLEANSING AN OCULAR REGION

CROSS-REFERENCE TO RELATED APPLICATION

This application is a divisional of U.S. patent application Ser. No. 14/707,187, filed May 8, 2015, which is a continuation-in-part of U.S. patent application Ser. No. 14/274,198, filed May 9, 2014, the contents of which are incorporated by reference herein.

FIELD OF THE INVENTION

Systems, methods, and kits useful for cleansing the eyelids and maintaining eyelid hygiene are disclosed.

BACKGROUND OF THE INVENTION

The eyelids are important to ocular health because they protect the eyes from airborne contaminants, such as pollen, dust particles or other foreign bodies. The eyelids contain several glands including the lacrimal glands and the specialized form of the sebaceous glands, the meibomian glands, which produce layers of tear film that are critical for healthy eyes.

The eyelids are subject to problems like blepharitis, dry eyes and inflammation of the meibomian glands. Another complication is the infestation of the arachnid, *Demodex folliculorum* (*Demodex* mites). The *Demodex* mite infestation is common in humans; anecdotal evidence suggests that the mites can be found in ten percent of the eyelashes of healthy persons. The occurrence of the infestation may also be age related.

*Demodex* mites reside inside the sebaceous glands and hair follicles. They cause damage to the cell walls by sucking nutrients from the hair roots. They burrow into the skin, lay eggs, introduce bacteria, and infect the skin. Some of the symptoms of infestation include itching and inflammation of the eyelids. Additionally, there is evidence that the mites can also be one of the causes of the skin disease rosacca.

SUMMARY OF THE INVENTION

Systems, methods, and kits useful for cleansing the eyelids and maintaining eyelid hygiene are disclosed. In one embodiment, a system for treating or cleansing an ocular region is disclosed. The system consists essentially of: (A) a tubular applicator, wherein the applicator comprises: (i) a first chamber and a second chamber; and (ii) a sealable element situated between the first chamber and the second chamber, wherein at least the second chamber is substantially pre-filled with an ocular composition, and (B) a dispenser, wherein the dispenser is bonded to an external surface of a first end of the applicator. In another embodiment, a method of treating or cleansing an ocular region is disclosed. The method includes (i) providing the system for treating or cleansing an ocular region; (ii) substantially filling at least the second chamber of the applicator with the ocular composition; and (iii) causing the sealable element to break such that the ocular composition is capable of flowing from the second chamber to the first chamber.

In yet another embodiment, a kit for treating or cleansing an ocular region is disclosed. The kit includes an enclosure for one or more of the systems for treating or cleansing an ocular region. Each of the systems may be individually wrapped.

In another embodiment, a kit for debridement of Anterior Blepharitis comprises an enclosure for housing: (i) one or more individually wrapped packages containing the system described above, wherein the ocular composition comprises polyhexamethylene biguanide, 1,2-hexanediol, 1,2-octanediol, D-panthenol, cocoamphodiacetate disodium, polyoxyethylene-80 sorbitan monolaurate, decyl polyglucoside, methyl gluceth-20, and PEG-120 methyl glucose dioleate; and (ii) a double-ended soft brush for removing debris from the eyelids and eyelashes.

In another embodiment, a method for treating Anterior Blepharitis includes: (i) providing the kit for debridement of Anterior Blepharitis; (ii) holding the applicator with the dispenser facing downward; (iii) applying pressure on a tip of the applicator that is opposite the dispenser to rupture the sealable element thereby enabling the ocular composition to saturate the dispenser; (iv) cleansing the surface of one or more of the eyebrows, closed eyelids and eyelashes by dispensing the ocular composition through the dispenser; (v) allowing the ocular composition to remain on the cleansed surface; and (vi) using the brush to remove any debris from the cleansed surface.

In yet another embodiment, a kit for treating of *Demodex* includes an enclosure for housing: (i) at least a first individually wrapped package containing the system described above, wherein the ocular composition comprises a first ocular composition, the first ocular composition comprising polyhexamethylene biguanide, 1,2-hexanediol, 1,2-octanediol, D-panthenol, cocoamphodiacetate disodium, polyoxyethylene-80 sorbitan monolaurate, decyl polyglucoside, methyl gluceth-20, and PEG-120 methyl glucose dioleate; (ii) at least a second individually wrapped package containing the system described above, wherein the ocular composition comprises a second ocular composition, the second ocular composition comprising a mixture of tea tree oil, sea buckthorn oil and a medium chain triglyceride; (iii) at least one of a double-ended soft brush or a pair of tweezers for removing debris from the eyelids and eyelashes; and (iv) one or more sterile saline wipes.

In another embodiment, a method for treating *Demodex* includes: (i) providing the kit for treating *Demodex*; (ii) holding the first individually wrapped package such that the dispenser end is pointed downward and pressing firmly on a tip of the applicator that is opposite the dispenser to rupture the sealable element thereby enabling the first ocular composition to saturate the dispenser; (iii) cleansing a surface of the eyebrows, closed eyelids and eyelashes by dispensing the first ocular composition through the dispenser; (iv) removing any debris from the area to be treated using either the brush or tweezers; (v) removing the first ocular composition by rinsing the cleansed surface; (vi) holding the second individually wrapped package such that the dispenser end is pointed downward and pressing firmly on a tip of the applicator that is opposite the dispenser to rupture the sealable element thereby enabling the second ocular composition to saturate the dispenser; and (vii) treating the cleansed surface by gently applying the second ocular composition to the cleansed surface. The method further comprises removing any additional debris from treated surface and further involves removing the second ocular composition. In another embodiment, the method for treating *Demodex*, further comprises repeating steps (i)-(iv), wherein the first ocular composition is allowed to remain on the cleansed surface.

In another embodiment, a kit for meibomian gland expression includes an enclosure for housing: (i) the system described above, wherein the ocular composition comprises polyhexamethylene biguanide, 1,2-hexanediol, 1,2-octanediol, D-panthenol, cocoamphodiacetate disodium, polyoxyethylene-80 sorbitan monolaurate, decyl polyglucoside, methyl gluceth-20, and PEG-120 methyl glucose dioleate; (ii) a pair of moist heat therapy goggles for combining moisture and heat to open up clogged meibomian glands by stimulating tear production and preventing evaporation of tears; (iii) one or more anesthetic gels; (iv) a paddle for expressing meibum from the meibomian glands; (v) a double-ended brush for removing debris from the eyelids and eyelashes; (vi) an eye wash for irrigating or flushing foreign bodies and debris from the eye; (vii) an eyelid cleanser for removing oil, debris and pollen from the eyelids; (viii) an eyelid spray containing vitamins A, C and E; and (ix) an ophthalmic emulsion to stabilize tear film and protect against moisture loss.

In another embodiment, a method for meibomian gland expression includes: (i) providing the kit for meibomian gland expression; (ii) instructing a patient to wear the moist heat therapy goggles for at least around 10-15 minutes in order to open up the clogged meibomian glands; (iii) applying the anesthetic gel to the eyes; (iv) after about 4-10 minutes, expressing the meibomian glands with the paddle; (v) cleansing closed eyelids to remove excessive sebum/oil from the eyelids by dispensing the ocular composition through the dispenser; (vi) removing debris from the cleansed eyelids using the brush; and (vii) irrigating out the eye using the eye wash.

BRIEF DESCRIPTION OF THE FIGURES

The features and advantages of certain embodiments will be more readily appreciated when considered in conjunction with the accompanying figures. The figures are not to be construed as limiting any of the preferred embodiments.

DETAILED DESCRIPTION

As used herein, an ocular region includes the eyes, eyelids, periorbital region or an area adjacent the eyes, eyelids and periorbital region. The periorbital region includes or relates to the tissues surrounding or lining the orbit of the eye. The orbit of the eye is the cavity of the skull in which the eye and related nerves and blood vessels are located.

Several compositions for cleansing or treating the ocular region are known in the art. These treatment compositions are usually applied to the ocular region by means of the finger tips, dispensers or applicators. Applicators can include swabs, Q-tips®, sponges, etc. In some instances, the fabric pads may be pre-soaked or pre-treated with a desired amount of treatment composition.

However, it has been observed that even these pre-treated applicators may not retain an optimal amount of the treatment composition. Seepage of the composition into the package(s) may cause a loss in the amount of the treatment composition retained in/by the applicator. The applicators or pre-treated fabric pads may also be inconvenient or messy to handle. For example, the treatment composition may be greasy, or drip from the applicator during use and may get on the fingers or clothes. Consequently, the overall efficacy of the treatment may be impacted.

Accordingly, for all the reasons stated above, there is a need for a mechanism to deliver a desired amount of an ocular composition to an ocular region. The mechanism should be convenient to use at home or in a doctor's office. The mechanism should facilitate a non-messy treatment of the ocular region.

Figure 1:
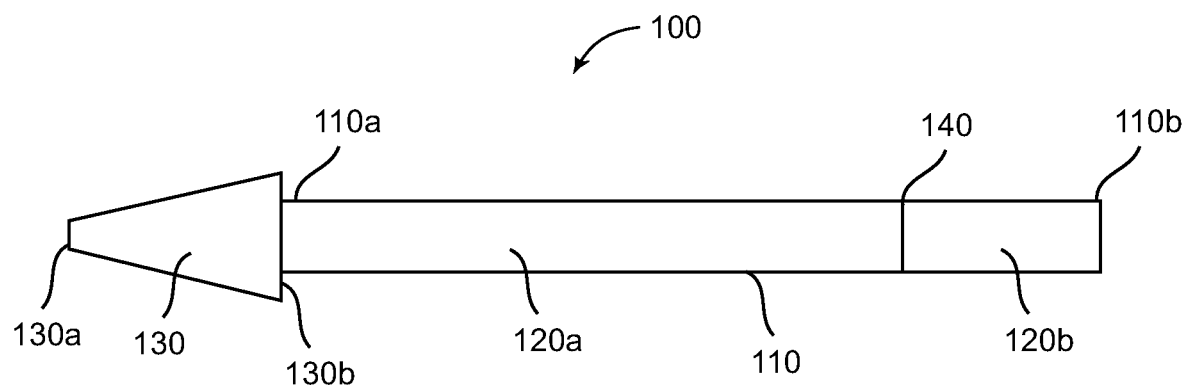
FIG. 1 depicts a system for treating or cleansing an ocular region according to one embodiment of the invention.

In one embodiment, a system suitable for both adjunctive eyelid therapy and hygiene maintenance is provided. Referring now to FIG. 1, in one embodiment of the invention, a system for cleansing or treating an ocular region 100 consists essentially of a tubular applicator 110 comprising a first chamber 120a and a second chamber 120b. A sealable element 140 is positioned between the first chamber 120a and the second chamber 120b. At least the second chamber 120b may be substantially pre-filled with an ocular composition. A dispenser 130 may be bonded to an external surface of a first end of the applicator 110a.

The applicator 110 may include a tubular enclosure or container. The applicator 110 may be manufactured of a suitable material known in the art. For example, the material may include plastic, polymer, resin, synthetic polymer and a composite material. In one embodiment, the applicator 110 may comprise a substantially clear polypropylene tube. Polypropylene is suitable and desirable material since it is lightweight, flexible and does not shatter. Polypropylene is also free of undesirable chemicals, such as, BPA. The applicator 110 may be dimensioned for convenient handling and such that it can hold a desired amount of the ocular composition. For example, the applicator 110 may have an external diameter that ranges from about 4 mm to about 8 mm and its length (that is, the distance between the first end 110a and the second end 110b) may range from about 75 mm to about 95 mm.

The applicator 110 includes an internal cavity that may be divided into the first chamber 120a and the second chamber 120b by an internal sealable element 140. As used herein, the term "chamber" is intended to encompass a compartment, enclosure or closed space. The sealable element 140 may be located substantially adjacent the second end of the applicator 110b. However, the sealable element 140 may also be located anywhere inside the applicator 110. For example, the sealable element 140 may be located substantially in the middle portion (not shown) of the applicator 110 or the sealable element 140 may be located substantially adjacent the first end of the applicator 110a (not shown). Accordingly, the first chamber 120a and the second chamber 120b may or may not be uniform in size. The sealable element 140 may include any mechanism known in the art that can be snapped, ruptured or broken, either completely or partially, by the application of pressure or an external force. For example, the sealable element 140 may include a membrane that can be broken by pressing the end 110b firmly.

A dispenser 130 is bonded to the first end of the applicator 110a. As used herein, the term "dispenser" is intended to include an object that dispenses or that allows the distribution of a desired amount of the ocular composition. The dispenser 130 may be made of an absorbent material that is self-saturating or pervious to the ocular composition and is also capable of retaining a desired amount of the ocular composition. For example, the dispenser 130 may include an absorbent material such as, foam, sponge, fiber, felt, cotton, rayon, synthetic foam, synthetic sponge, textile and synthetic fiber. In one embodiment, the dispenser 130 may be rectangular shaped and may be made of 100PPI medical grade foam. The dispenser 130 may be dimensioned to receive a desired amount of the ocular composition through an opening (not shown) at the first end of the applicator 110a. In one embodiment, the dispenser 130 may range from about 15 mm to about 20 mm in diameter and its length (that is, the distance between the first end of the dispenser 130a and the second end of the dispenser 130b) may range from about 30 mm to about 40 mm. The dispenser 130 may substantially envelope the opening at the first end of the applicator 110a.

The ocular composition can be in a form chosen from an emulsion, a suspension, a dispersion, a foam, a cream, a lotion, a solution, a paste, a gel or a spray. The ocular composition may be capable of cleansing the ocular region or treating the ocular region. The ocular composition may be a non-irritating liquid composition useful in cleansing the eyelids. The ocular composition may also be effective as an eyelid cleanser, as it has an antimicrobial effect. The use of non-irritating ingredients that also exhibit antimicrobial benefits in the ocular composition increases its cleansing ability. The ocular compositions may offer convenient combination therapy for improving overall eyelid hygiene and also providing for adjunctive eyelid therapy.

For example, the ocular composition may include a surfactant mixture comprising PEG-80 sorbitan laurate, sodium trideceth sulphate, PEG-150 distearate, cocamidopropylhydroxy sultaine, lauroamphocarboxy glycinate, and sodium laureth-13 carboxylate, the surfactant mixture present in a concentration of 7-10%; PEG-15 tallow polyamine present in a concentration of 0.1-0.5%; sodium chloride present in a concentration of 0.6-0.9%, at least one microbiological preservative selected from the group consisting of Quaternium-15 and benzyl alcohol present in concentration of 0.1-0.5% and a chelating agent present in a concentration of 0-0.1%.

In another embodiment, the ocular composition may include the eyelid scrub composition disclosed in U.S. Pat. No. 7,951,387 assigned to OCuSOFT, Inc. The contents of this patent are incorporated in their entireties. For example, the ocular composition comprises PHMB, 1,2-hexanediol, and 1,2-octanediol in combination with a pH stabilizing surfactant solution. Suitable surfactants to be used in the pH stabilizing surfactant solution include amphoteric surfactants, anionic surfactants, and nonionic surfactants. Suitable amphoteric surfactants include, but are not limited to alkyldimethyl betaines, alkylamido betaines, sulfobetaines, and imidazoline amphoterics. Suitable anionic surfactants include, but are not limited to fatty alcohol sulfates, alpha olein sulfonates, sulfosuccinates, sarcosinates, phosphate esters, and carboxylates. Suitable nonionic surfactants include, but are not limited to alkanolamids, ethoxylate amids, esters, aixylated alcohols, alkylpolyglucosides, amine oxides, sorbitan esters, and ethoxylates. The pH stabilizing surfactant solution comprises cocoamphodiacetate disodium, polyoxyethylene 80 sorbitan monolaurate, decyl polyglucoside, and a modified Ringer's solution. Cocoamphodiacetate disodium is an amphoteric surfactant. Polyoxyethylene 80 sorbitan monolaurate and decyl polyglucoside are both nonionic surfactants. In another embodiment, the composition, when mixed, comprises about 0.1 to 25 wt. % cocoamphodiacetate disodium, 0.1 to 10 wt. % polyoxyethylene 80 sorbitan monolaurate, 0.2 to 10 wt. % decyl polyglucoside, and 60 to 98 wt. % modified Ringer's solution. The modified Ringer's solution comprises, sodium chloride, potassium chloride, calcium chloride, and water. Preferably, the water used is purified water. The modified Ringer's solution may also comprise 0.05 to 1.2 wt. % sodium chloride, 0.005 to 0.5 wt. % potassium chloride, 0.005 to 0.5 wt. % calcium chloride, and water. In still another embodiment, the modified Ringer's solution comprises about 0.7 wt. % sodium chloride, about 0.03 wt. % potassium chloride, about 0.033 wt. % calcium chloride, and purified water.

The ocular composition can further comprise one or more moisturizers. Moisturizers are chemicals that prevent transepidermal water loss. Moisturizers may prevent water loss by forming a film over the skin to prevent water from evaporating from the skin. Alternatively, moisturizers comprise hydroscopic molecules that draw water from the air into the skin. Suitable moisturizers include, but are not limited to, methyl gluceth-20, sorbital, glycerine, propylene glycol, carboxylates, amino acids, glucoside derivatives, urea, lactates, and derivatives of pantothenic acid. Examples of derivatives of pantothenic acid include panthenol, D-panthenol, and D, L-panthenol.

The ocular composition may also include a foam stabilizer. A foam stabilizer is a chemical which increases the lifetime of the foam. The foam stabilizer can be a polyethylene glycol diester of methyl glucose and a fatty acid. Suitable fatty acids include oleic acid, steric acid, lauric acid, caprylic acid, and capric acid. Suitably, the foam stabilizer is PEG-120 methyl glucose dioleate.

One specific embodiment of the ocular composition comprises polyhexamethylene biguanide, 1,2-hexanediol, 1,2-octanediol, D-panthenol, cocoamphodiacetate disodium, polyoxyethylene-80 sorbitan monolaurate, decyl polyglucoside, methyl gluceth-20, and PEG-120 methyl glucose dioleate.

Another specific embodiment of the ocular composition comprises about 0.02 wt. % to about 0.3 wt. % PHMB, about 0.05 wt. % to about 2.0 wt. % 1,2-hexanediol, about 0.05 wt. % to about 2.0 wt. % 1,2-octanediol, about 0.1 wt. % to about 25 wt. % cocoamphodiacetate disodium, about 0.1 wt. % to about 10 wt. % polyoxyethylene 80 sorbitan monolaurate, about 0.2 wt. % to about 10 wt. % decyl polyglucoside, and about 60 wt. % to about 98 wt. % Modified Ringer's Solution.

Yet another specific embodiment of the ocular composition comprises about 0.04 wt. % polyhexamethylene biguanide, about 0.2 wt. % 1,2-hexanediol, about 0.2 wt. % 1,2-octanediol, about 0.2 wt. % D-panthenol, about 0.215 wt. % cocoamphodiacetate disodium, about 4.032 wt. % polyoxyethylene 80 sorbitan monolaurate, about 0.275 wt. % decyl polyglucoside, about 4.3 wt. % methyl gluceth-20, about 0.6 wt. % PEG-120 methyl glucose dioleate, about 87.985 wt. % Modified Ringer's Solution, and water.

Zinc salts are astringents which cause skin to tighten. The skin around the ocular area is more sensitive that other areas of skin. The inclusion of a zinc salt is a composition may be undesirable as its astringent property would make the composition more irritating to the eyelid area. Therefore in one embodiment, the ocular composition comprises PHMB, 1,2-hexanediol, 1,2-octanediol, and a pH stabilizing surfactant solution, but is also essentially free of zinc salts. Examples of zinc salts include zinc acetate, zinc lactate, zinc gluconate, zinc citrate, zinc butyrate, and zinc sterate.

Figure 2A:
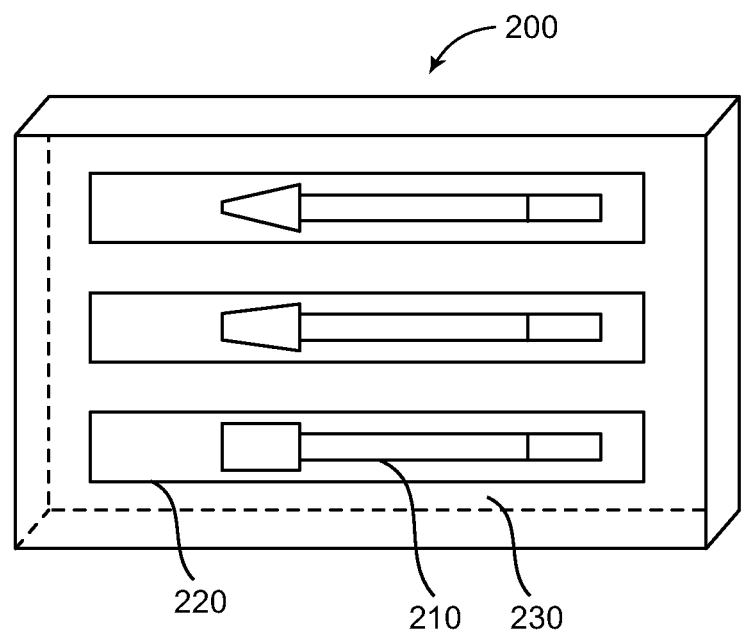
FIGS. 2A and 2B depict kits for treating or cleansing an ocular region according to one embodiment of the invention.
Figure 2B:
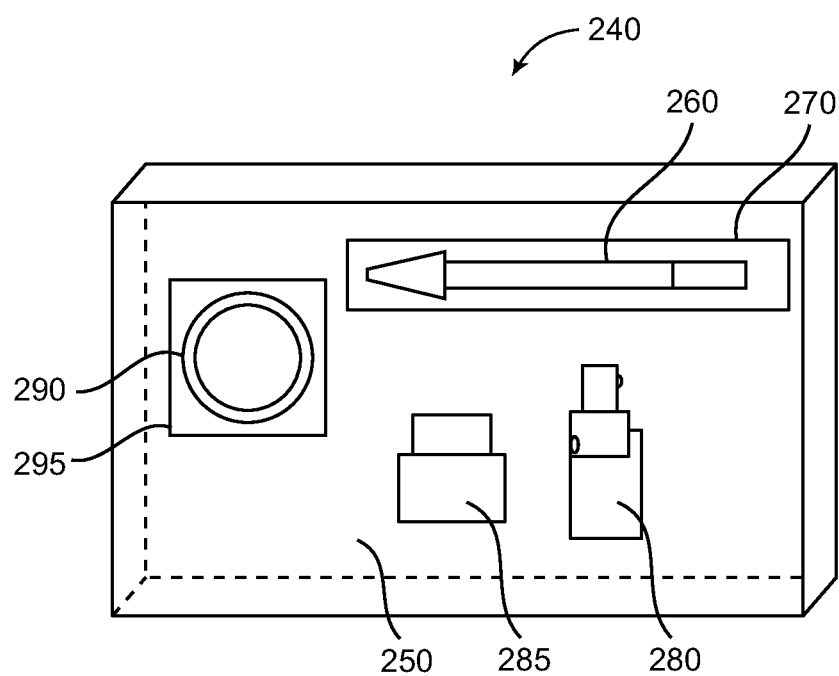

In another embodiment of the invention, a kit 200 for debridement of Anterior Blepharitis is disclosed. As shown in FIG. 2A, the kit 200 may include an enclosure or housing 230. The enclosure 230 may be made of paper, plastic or another suitable material known in the art. One or more systems 210 for treating an ocular region (100) described earlier may be packaged within the enclosure 230. Each of the systems 230 may be further individually wrapped 210. The individually wrapped 210 packaging may further include an ocular composition comprising polyhexamethylene biguanide, 1,2-hexanediol, 1,2-octanediol, D-panthenol, cocoamphodiacetate disodium, polyoxyethylene-80 sorbitan monolaurate, decyl polyglucoside, methyl gluceth-20, and PEG-120 methyl glucose dioleate. The kit 200 for debridement of Anterior Blepharitis may further include a specialized double-ended soft brush (not shown) for removing scurf and debris from the eyelids and eyelashes.

In yet another embodiment, a method for treating a patient having Anterior Blepharitis using the above-described kit for debridement of Anterior Blepharitis is disclosed. The patient can be treated in a doctor's office, such as, an ophthalmologist's office. The method involves the following steps: 1) providing one or more individually wrapped packages containing the system described herein, wherein the system comprises a combination of an applicator and an composition comprising polyhexamethylene biguanide, 1,2-hexanediol, 1,2-octanediol, D-panthenol, cocoamphodiacetate disodium, polyoxyethylene-80 sorbitan monolaurate, decyl polyglucoside, methyl gluceth-20, and PEG-120 methyl glucose dioleate; 2) with the system still contained within the packaging, holding the applicator with the dispenser facing downward; 3) with the system still contained within the packaging, pressing firmly on the tip of the applicator at the end that is opposite the dispenser to rupture the sealable element to enable the ocular composition to saturate the dispenser; 4) removing the applicator from the packaging; 5) using the applicator as an handle, cleansing an area to be treated, for instance, the eyebrows, closed eyelids and eyelashes by dispensing the ocular composition through the dispenser; 6) allowing the ocular composition to remain on the area to be treated (that is, the area to be treated is not rinsed); and 7) removing any scurf or debris from the area to be treated. For example, a specialized brush can be used to remove the scurf or debris.

According to another embodiment, a method for ongoing maintenance of an area treated for Anterior Blepharitis involves the following steps: 1) cleansing the area treated in the doctor's office daily with an ocular composition dispensed in pre-moistened pads or as a cleanser (for example, OCuSOFT® Lid Scrub® PLUS pre-moistened pads or Foaming Eyelid Cleanser), for at least the first two weeks post-treatment in the doctor's office; 2) using the ocular composition daily for routine eyelid hygiene; 3) applying an eyelid spray (for example, Tears Again® ADVANCED Eyelid Spray) throughout the day, as needed, to soothe red, irritated eyelids; and 4) stabilizing the lipid layer of the tear film of the eye by applying an ophthalmic emulsion (for example, Retaine MGD® ophthalmic emulsion). The method further involves scheduling a follow-up appointment with the doctor for a second treatment, if required.

In yet another embodiment, the ocular composition may include a mixture of tea tree oil, sea buckthorn oil and a medium chain triglyceride. Such a composition has been found effective in treating *Demodex* mites. The composition has been disclosed in U.S. Pat. Pub. No. 20120121694, the contents of which have been incorporated by reference herein. The medium chain triglyceride may comprise caprylic capric triglyceride or any other suitable dermatological carrier for the tea tree oil and sea buckthorn oil. For example, in one or more embodiments, the ocular composition may comprise about 45% to about 55% tea tree oil, about 15% to about 25% sea buckthorn oil, and about 25% to about 35% caprylic capric triglyceride. In another embodiment, the ocular composition may include 50% tea tree oil, 20% sea buckthorn oil, and 30% caprylic capric triglyceride.

In another embodiment of the invention, a kit 200 for treatment of *Demodex* is disclosed. As shown in FIG. 2A, the kit 200 may include an enclosure or housing 230. The enclosure 230 may be made of paper, plastic or another suitable material known in the art. One or more systems 210 for treating an ocular region (100) described earlier may be packaged within the enclosure 230. Each of the systems 230 may be further individually wrapped 210. At least one of the individually wrapped 210 packages may further include a first ocular composition comprising polyhexamethylene biguanide, 1,2-hexanediol, 1,2-octanediol, D-panthenol, cocoamphodiacetate disodium, polyoxyethylene-80 sorbitan monolaurate, decyl polyglucoside, methyl gluceth-20, and PEG-120 methyl glucose dioleate. At least one of the individually wrapped 210 packages may include a second ocular composition comprising a mixture of tea tree oil, sea buckthorn oil and a medium chain triglyceride.

The kit 200 for treating *Demodex* may further include a specialized double-ended soft brush (not shown) for removing scurf and debris from the eyelids and eyelashes.

The kit 200 for treating *Demodex* may further include a pair of tweezers (not shown) for removing scurf and debris from the eyelids and eyelashes. The tweezers may have a cone tip and may be manufactured from plastic.

The kit 200 for treating *Demodex* may further include one or more sterile saline wipes. The wipes may be individually wrapped to provide safe and gentle cleansing of the eye area while eliminating the risk of cross-contamination.

In another embodiment, a method for treating a patient having *Demodex* using the above-described kit for treatment of *Demodex* is disclosed. The patient can be treated in a doctor's office, such as, an ophthalmologist's office. The method involves the following steps: 1) providing at least one individually wrapped package containing the system described herein, wherein the system comprises a combination of an applicator and a first ocular composition comprising polyhexamethylene biguanide, 1,2-hexanediol, 1,2-octanediol, D-panthenol, cocoamphodiacetate disodium, polyoxyethylene-80 sorbitan monolaurate, decyl polyglucoside, methyl gluceth-20, and PEG-120 methyl glucose dioleate; 2) with the system still contained within the packaging, holding the applicator with the dispenser facing downward; 3) with the system still contained within the packaging, pressing firmly on the tip of the applicator at the end that is opposite the dispenser to rupture the sealable element to enable the first ocular composition to saturate the dispenser; 4) removing the applicator from the packaging; 5) using the applicator as an handle, cleansing an area to be treated, for instance, the eyebrows, closed eyelids and eyelashes by dispensing the first ocular composition through the dispenser; 6) removing any debris from the area to be treated (for instance, a specialized brush or tweezers can be used); 7) removing the first ocular composition by rinsing the eye area (for instance, with OCuSOFT® Eye wash or the sterile saline wipes); 8) providing at least one individually wrapped package containing the system described herein, wherein the system comprises a combination of an applicator and a second ocular composition comprising a mixture of tea tree oil, sea buckthorn oil and a medium chain triglyceride; 9) with the system still contained within the packaging, holding the applicator with the dispenser facing downward; 10) with the system still contained within the packaging, pressing firmly on the tip of the applicator at the end that is opposite the dispenser to rupture the sealable element to enable the second ocular composition to saturate the dispenser; 11) removing the applicator from the packaging; 12) using the applicator as an handle, gently applying the second ocular composition to an area to be treated, for instance, the eyebrows, closed eyelids and eyelashes with the dispenser end of the applicator taking special care to avoid direct contact with the eye; 13) removing any additional debris from the area to be treated (for instance, a specialized brush or tweezers can be used); 14) removing the second ocular composition by rinsing the eye area (for instance, with OCuSOFT® Eye wash or the sterile saline wipes). In another embodiment, after step 14, steps 1-6 can be repeated and the first ocular composition can be allowed to remain on the area to be treated.

According to another embodiment, a method for ongoing maintenance of an area treated for *Demodex* involves the following steps: 1) cleansing the area treated in the doctor's office daily with the first ocular composition dispensed in pre-moistened pads or as a cleanser (for example, OCu-SOFT® Lid Scrub® PLUS pre-moistened pads or Foaming Eyelid Cleanser), for at least the first two weeks post-treatment in the doctor's office; 2) using a third ocular composition (for example, OCuSOFT® Lid Scrub® Original pre-moistened pads or Foaming Eyelid Cleanser) daily for routine eyelid hygiene; 3) stabilizing the lipid layer of the tear film of the eye by applying an ophthalmic emulsion (for example, Retaine® MGD® ophthalmic emulsion); and 4) applying an ointment (for instance, Retaine® PM® Nighttime Ointment) for added night time relied. The method further involves scheduling a follow-up appointment with the doctor for a second treatment, if required.

In yet another embodiment, the ocular composition consists essentially of purified water, PEG-80 sorbitan laurate, sodium trideceth sulfate, PEG-150 distearate, sodium lauroamphoacetate, cocamidopropyl hydroxysultaine, sodium laureth-13 carboxylate, sodium chloride, PEG-15 cocopolyamine, polyhexamethylene biguanide, potassium sorbate, 1,2 hexanediol, and caprylyl glycol.

Although various exemplary ocular compositions have been described herein, the compositions disclosed herein are not intended to be limiting. In fact, any composition that can be used to cleanse or treat the eyes, eyelids, or an ocular region, may be used in accordance with the various embodiments of the invention.

As described earlier, the sealable element 140 may be snapped broken or ruptured by the application of pressure. For example, the sealable element 140 may be conveniently snapped by a user of the system 100. Upon breaking the sealable element 140, a substantially contiguous opening is created between the first chamber 120a and the second chamber 120b in the applicator 110. This allows a passage for the ocular composition from the second chamber 120b to the first chamber 120a.

The first end 110a of the applicator 110 further includes an opening (not shown). The breaking of the sealable element 140 allows the ocular composition to flow through the opening such that it can be dispensed from the dispenser 130. In another embodiment, the tubular applicator does not include a sealable element. The ocular composition is contained within the undivided chamber of the applicator (not shown). Upon pressing the tip of the tubular applicator that is at an opposing end to the dispenser, the ocular composition can be seamlessly pushed into the dispenser where it can saturate the absorbent material of the dispenser and thereby be dispensed to an area that requires cleansing or treatment.

In another embodiment of the invention, a method of treating or cleansing an ocular region is disclosed. The method includes the steps of providing the system (described earlier) for treating or cleansing an ocular region; (ii) substantially filling at least the second chamber of the applicator with the ocular composition; and (iii) causing the sealable element to break such that the ocular composition is capable of flowing from the second chamber to the first chamber. The method may further involve pre- or post-cleansing of the treatment area and follow-up treatment of the treatment area.

In yet another embodiment of the invention, a kit 240 for treating or cleansing an ocular region is disclosed. The kit 240 may include an enclosure or housing 250. The enclosure 250 may be made of paper, plastic or another suitable material known in the art. One or more systems 260 for treating an ocular region (100, 210) described earlier may be packaged within the enclosure 250. Each of the systems 260 may be further individually wrapped 270. The kit 240 may further include at least a sealable container 295 enclosing one or more fabric pads 290. The fabric pad 290 must be selected so that the fabric is capable of containing the ocular composition in the interstitial spaces of the fabric's weave. In one aspect, the fabric pad 290 comprises two sheets of fabric, a first sheet of fabric and a second sheet of fabric. The two pieces may be held together by stitching them together on the sides. The fabric pad 290 can have a surface area dimensioned to receive an effective amount of the ocular composition. In one aspect, the pre-moistened fabric pad 290 comprises a lint-free non-abrasive rayon and polypropylene fabric blend. In another aspect, the fabric pad 290 comprises a textured surface to absorb and retain the ocular composition. However, the fabric pad 290 must remain soft enough so as to not be harsh on the user's skin. Preferably, the fabric pads 290 further comprise a moisturizer blend that is non-drying and non-irritating.

The individually wrapped packages or sealable container 295 may be made of any suitable material including paper, plastic or a metal foil material. The pre-moistened fabric pads 290 may be individually packaged for convenience. In one aspect, the sealable container 295 may be an impervious wrapper so that the fabric pad 290 with the ocular composition does not come into contact with contaminants and remains moistened for a long period of time. The pre-moistened fabric pads 290 are applied to the eyelids or scrubbed using lateral side to side strokes on to the eyelids and other perioocular regions that need to be cleansed or treated. The eyelids are rinsed with water and the used fabric pads 290 are discarded.

The moisture pads 290 may be soaked in an ocular cleansing solution for convenience in cleansing the eyelids. The kit 240 may further include a first receptacle 285 containing an ocular composition and a second receptacle 280 containing a foaming ocular composition. The first and second receptacles 285, 280 may be selected from a glass bottle, a plastic bottle, or other suitable material known in the art. For convenience and economy, the receptacles 285, 280 may range in size from about 30 ml to 480 ml.

The kits 200, 240 may further include instructions. The instructions can be printed in a manual included in the kits 200, 240 on instruction sheets or they may be printed directly on the enclosures 230, 250. If the instructions are printing on the enclosures 230, 250, they may be printed on the outside of the enclosures 230, 250 or on the inside of the enclosures 230, 250 where the instructions are not visible to the user of the kits 200, 240 until the user opens the kits 200, 240. As an alternative, the instructions may be printed on the containers or packaging of the individual components of the eyelid treatment kit, such as, 220.

In yet another embodiment, a kit for meibomian gland expression (or Posterior Blepharitis) is provided. As shown in FIG. 2A, the kit 200 may include an enclosure or housing 230. The enclosure 230 may be made of paper, plastic or another suitable material known in the art. One or more systems 210 for treating an ocular region (100) described earlier may be packaged within the enclosure 230. Each of the systems 230 may be further individually wrapped 210. The individually wrapped 210 packaging may further include an ocular composition comprising polyhexamethylene biguanide, 1,2-hexanediol, 1,2-octanediol, D-panthenol, cocoamphodiacetate disodium, polyoxyethylene-80 sorbitan monolaurate, decyl polyglucoside, methyl gluceth-20, and PEG-120 methyl glucose dioleate.

The meibomian gland expression kit 200 may further include a pair of moist heat therapy goggles (not shown). The goggles can combine moisture and heat to open the clogged meibomian glands that contribute to inflammation and Dry Eye discomfort. The goggles can provide a comfort seal around the eyes to help stimulate tear production and prevent the evaporation of tears.

The meibomian gland expression kit 200 may further include one or more anesthetic gels (not shown). The gels may have a high viscosity to improve patient comfort and increase efficiency in the operating room or the clinic.

The meibomian gland expression kit 200 may further include a device (not shown), such as a paddle, to gently and effectively express meibum from the meibomian glands. When the paddle device is positioned behind the anesthetized eyelid parallel to the glands, the application of gentle digital pressure on the outer lid prompts the meibum to egress.

The meibomian gland expression kit 200 may further include a specialized double-ended brush (not shown) for removing scurf and debris from the eyelids and eyelashes.

The meibomian gland expression kit 200 may further include an eye wash (not shown) for irrigating or flushing foreign bodies and debris from the eye. The eyewash may include a purified water and sodium chloride ophthalmic irrigating solution, such as, OCuSOFT® Eye Wash.

The meibomian gland expression kit 200 may further include an eyelid cleanser (not shown) for removing oil, debris and pollen from the eyelids (not shown). The eyelid cleansers may comprise pre-moistened pads or as foaming cleansers.

The meibomian gland expression kit 200 may further include an eyelid spray. The eyelid spray may include liposomes containing vitamins A, C and E to soothe eyelid irritation while improving tear break up time (TBUT) and tear film stability.

The meibomian gland expression kit 200 may further include an ophthalmic emulsion. The ophthalmic emulsion can include a lipid-replenishing formula that utilizes electrostatic attraction to stabilize tear film and protect against moisture loss.

In yet another embodiment, a method for meibomian gland expression using the above-described meibomian gland expression kit is disclosed. The patient can be treated in a doctor's office, such as, an ophthalmologist's office. The method involves the following steps: 1) instructing the patient to wear the moist heat therapy goggles for at least around 10-15 minutes in order to open up the clogged meibomian glands; 2) anesthetizing the eyes with the anesthetic gel; 3) after waiting for around 4-10 minutes, expressing the meibomian glands with the paddle devices; 4) providing one or more individually wrapped packages containing the system described herein, wherein the system comprises a combination of an applicator and a composition comprising polyhexamethylene biguanide, 1,2-hexanediol, 1,2-octanediol, D-panthenol, cocoamphodiacetate disodium, polyoxyethylene-80 sorbitan monolaurate, decyl polyglucoside, methyl gluceth-20, and PEG-120 methyl glucose dioleate; 5) with the system still contained within the packaging, holding the applicator with the dispenser facing downward; 6) with the system still contained within the packaging, pressing firmly on the tip of the applicator at the end that is opposite the dispenser to rupture the sealable element to enable the ocular composition to saturate the dispenser; 7) removing the applicator from the packaging; 8) using the applicator as an handle, cleansing an area to be treated, for instance, the closed eyelids to remove excessive sebum/oil from the eyelids by dispensing the ocular composition through the dispenser; 9) removing any scurf or debris from the area to be treated using the specialized brush; and 10) irrigating out the eye using the eye wash.

According to another embodiment, a method for ongoing maintenance of an area treated for meibomian gland expression involves the following steps: 1) using the moist heat therapy goggles daily to open the meibomian glands; 2) cleansing the area treated in the doctor's office daily with an ocular composition dispensed in pre-moistened pads or as a cleanser (for example, OCuSOFT® Lid Scrub® PLUS pre-moistened pads or Foaming Eyelid Cleanser), for at least the first two weeks post-treatment; 2) using the ocular composition daily for routine eyelid hygiene; 3) using a third ocular composition (for example, OCuSOFT® Lid Scrub® Original pre-moistened pads or Foaming Eyelid Cleanser) daily for routine eyelid hygiene; 4) applying an eyelid spray (for example, Tears Again® ADVANCED Eyelid Spray) throughout the day, as needed, to soothe red, irritated eyelids; and 5) stabilizing the lipid layer of the tear film of the eye by applying an ophthalmic emulsion (for example, Retaine® MGD® ophthalmic emulsion). The method further involves scheduling a follow-up appointment with the doctor for a second treatment, if required.

It should be understood that, as used herein, "first," "second," etc., are arbitrarily assigned and are merely intended to differentiate between two or more compartments, compositions etc., and does not indicate any particular orientation or sequence. Furthermore, it is to be understood that the mere use of the term "first" does not require that there be any "second," and the mere use of the term "second" does not require that there be any "third," etc.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is, therefore, evident that the particular illustrative embodiments disclosed above may be altered or modified and all such variations are considered within the scope and spirit of the present invention. While kits, compositions and methods are described in terms of "comprising," "containing," or "including" various components or steps, the kits, compositions and methods also can "consist essentially of" or "consist of" the various components and steps. Whenever a numerical range with a lower limit and an upper limit is disclosed, any number and any included range falling within the range is specifically disclosed. In particular, every range of values (of the form, "from about a to about b," or, equivalently, "from approximately a to b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent(s) or other documents that may be incorporated herein by reference, the definitions that are consistent with this specification should be adopted.

The invention claimed is:

1. A method for treating Anterior Blepharitis comprising:
providing a kit for treating Anterior Blepharitis, the kit comprising:
one or more individually wrapped packages containing a system for treating or cleansing an ocular region, the system comprising:
a tubular applicator segmented into a first chamber and a second chamber by a single sealable element, wherein the second chamber contains an ocular composition, and
wherein upon breaking the sealable element, the ocular composition flows from the second chamber to the first chamber, and
a self-saturating dispenser for the ocular composition, wherein the dispenser is bonded to an external surface of a first end of the container,
wherein the ocular composition comprises polyhexamethylene biguanide, 1,2-hexanediol, 1,2-octanediol, D-panthenol, cocoamphodiacetate disodium, polyoxyethylene-80 sorbitan monolaurate, decyl polyglucoside, methyl gluceth-20, and PEG-120 methyl glucose dioleate;
holding the applicator with the dispenser facing downward;
applying pressure on a tip of the applicator that is opposite the dispenser to rupture the sealable element thereby enabling the ocular composition to saturate the dispenser;
cleansing an ocular region by dispensing the ocular composition through the dispenser; and
allowing the ocular composition to remain on the cleansed surface.

2. The method according to claim 1, further comprising using a double-ended soft brush to remove any debris from the cleansed surface.

3. A method for treating *Demodex* comprising:
providing a kit for debridement of *Demodex*, the kit comprising:
a first individually wrapped package containing a system for treating or cleansing an ocular region, the system comprising:
a tubular applicator segmented into a first chamber and a second chamber by a single sealable element, wherein the second chamber contains an ocular composition, and
wherein upon breaking the sealable element, the ocular composition flows from the second chamber to the first chamber, and
a self-saturating dispenser for the ocular composition, wherein the dispenser is bonded to an external surface of a first end of the container,
wherein the second chamber is substantially pre-filled with a first ocular composition, and wherein the first ocular composition comprises polyhexamethylene biguanide, 1,2-hexanediol, 1,2-octanediol, D-panthenol, cocoamphodiacetate disodium, polyoxyethylene-80 sorbitan monolaurate, decyl polyglucoside, methyl gluceth-20, and PEG-120 methyl glucose dioleate,
holding the applicator such that the dispenser end is pointed downward and pressing firmly on a tip of the applicator that is opposite the dispenser to rupture the sealable element thereby enabling the first ocular composition to saturate the dispenser, and
cleansing an ocular region by dispensing the first ocular composition through the dispenser.

4. The method according to claim 3, further comprising removing any debris from the area to be treated using either a double-ended soft brush or a pair of tweezers.

5. The method according to claim 4, further comprising removing the first ocular composition by rinsing the cleansed surface.

6. The method according to claim 5, further comprising applying a second ocular composition to the cleansed surface, the second ocular composition comprising a mixture of tea tree oil, sea buckthorn oil and a medium chain triglyceride.

7. The method according to claim 6, further comprising removing any additional debris from treated surface.

8. The method according to claim 6, further comprising removing the second ocular composition from the cleansed surface.

9. The method according to claim 4, wherein the first ocular composition is allowed to remain on the cleansed surface.

* * * * *